US00PP15910P3

(12) United States Plant Patent
Hirose

(10) Patent No.: US PP15,910 P3
(45) Date of Patent: Aug. 9, 2005

(54) *ACER PALMATUM* PLANT NAMED 'FUJINAMI NISHIKI'

(50) Latin Name: *Acer palmatum*
Varietal Denomination: Fujinami Nishiki

(75) Inventor: Yoshimichi Hirose, Iwakuni (JP)

(73) Assignee: Hines Nurseries, Inc., Irvine, CA (US)

( * ) Notice: Subject to any disclaimer, the term of this patent is extended or adjusted under 35 U.S.C. 154(b) by 311 days.

(21) Appl. No.: 10/107,904

(22) Filed: Mar. 26, 2002

(65) Prior Publication Data

US 2003/0188355 P1 Oct. 2, 2003

(51) Int. Cl.[7] ..... A01H 5/00
(52) U.S. Cl. ..... Plt./224
(58) Field of Search ..... Plt./224

*Primary Examiner*—Anne Marie Grunberg
(74) *Attorney, Agent, or Firm*—Christie, Parker & Hale, LLP

(57) ABSTRACT

A new plant variety of *Acer palmatum* characterized by red sectoral leaf variegation.

1 Drawing Sheet

Classification: The present invention relates to a new *Acer palmatum* Thunb. plant.

Varietal denomination: The new plant has the varietal denomination 'Fujinami Nishiki'.

BACKGROUND OF THE INVENTION

The present invention relates to a new and distinct variety of *Acer palmatum* Thunb., which was discovered as a branch sport of an unnamed variety of *Acer palmatum* (unpatented) in Kawaguchi City, Saitama, Japan, by the originator, Mr. Yoshimichi Hirose. The varietal denomination of the new variety is 'Fujinami Nishiki'.

The genus *Acer* is included in the family Aceraceae that comprises 2 genera of shrubs and trees native to northern temperate regions and tropical mountains. *Acer* comprises about 150 species of deciduous or evergreen trees and shrubs, native to North and Central America, Europe, North Africa and Asia.

*Acer palmatum* is a native of Japan and Korea. *Acer palmatum* generally has 5 to 7 lobed, palmate leaved, lobes that are deeply divided, lanceolate to oblong, biserrate, cuspidate. Petioles are approximately 4 cm long.

SUMMARY OF THE INVENTION

The new variety was discovered as a branch sport and differs from other cultivars known to the inventor by its red sectoral leaf variegation. Asexual reproduction of the new variety by grafting conducted in Saitama Prefecture, Japan and Forest Grove, Oreg., has confirmed that the distinctive characteristics of the new variety are stable and transmitted to succeeding generations and that the new variety reproduces true to type.

COMPARISON WITH PARENT

'Fujinami Nishiki' is distinguished from its parent and all other varieties of *Acer palmatum* of which I am aware by its red sectoral leaf variegation. In contrast, the parent of 'Fujinami Nishiki' exhibits all red foliage.

BRIEF DESCRIPTION OF ILLUSTRATION

The accompanying photographic illustration shows a plant of the new cultivar as true to color as is reasonably possible to make in an illustration of this character.

This illustration shows the distinctive leaf variegation of the new variety.

DESCRIPTION OF THE NEW VARIETY

*Acer palmatum* 'Fujinami Nishiki' has not been observed under all possible environmental, cultural and light conditions. The following observations and descriptions are of 4 year-old plants grown in 5-gallon nursery containers in Forest Grove, Oreg., Lewisberry, Pa., and Kawaguchi City, Saitama, Japan. Phenotypic expression may vary with light intensity, cultural, and environmental conditions. In this description, color references are to The Royal Horticultural Society Colour Chart (2001) and terminology used in the color descriptions herein refers to plate numbers in this color chart. As with many plants in the Aceraceae family, phenotypic characteristics can be dramatically different in terms of growth morphology.

CLASSIFICATION

Botanical: *Acer palmatum* 'Fujinami Nishiki' Thunb.

Parentage: Branch sport of an unnamed, unpatented variety of *Acer palmatum.*

*Propagation.*—Grafting.

Plant:

*Size.*—8 to 10 meters tall at maturity.

*Branching.*—Typical Number of Branches: More than 1000. Observed Number of Branches: 15. Branch Size: Approximately 1 meter. Branch Diameter: Base: 3 cm. Apex: less than 1 cm. Branch Coloration: Near Purple Group 77A.

*Habit.*—Upright, oval.

Leaf:

*Shape.*—5 lobed, palmate.

*Apex.*—Acute.

*Base.*—Obtuse.

*Margin.*—Serrated.

*Texture.*—Moderately firm.

*Substance.*—Chartaceous.

*Pattern of variegation.*—Sectoral; most commonly 1 to 3 lobes of leaf entirely reddish in color; occasional lobes in which irregularly alternating patterns of ground color and variegation within or bounded by veins; or occasional leaves that are entirely of ground color or variegation color; in general, the percentage of the variegated portion of the leaf is 10% to 35%. Leaf Color: Varies with intensity of sunlight and cultural conditions; the following color readings were taken in Forest Grove, Oreg. of a 4 year-old specimen grown in 5 gallon nursery containers. Upper side: Ground color near Purple Group 79A to 79B; variegation near Red Group 50A. Underside: Ground color near Purple Group 79A to 79B; variegation near Red Group 50B. Venation Upper Surface: Midvein depressed. Under Surface: Midvein slightly raised. Color: Variegated sectors near Red-Purple 71A; ground color sector near Red Group 50A.

*Petioles.*—Size: 3.5 cm long. Color: Near Red Group 46A.

*Internodes.*—3 to 4 cm long.

*Leaf size.*—From 4 to 7 cm long and 6 to 8 cm wide.

Hardiness: USDA Zone 5 (20° to 10° F.).

Vigor: Slow.

Pests/diseases: None noted.

Infloresence: None yet observed.

Reproductive organs: None yet observed.

I claim:

1. A new variety of *Acer palmatum* plant named 'Fujinami Nishiki' substantially as described and illustrated.

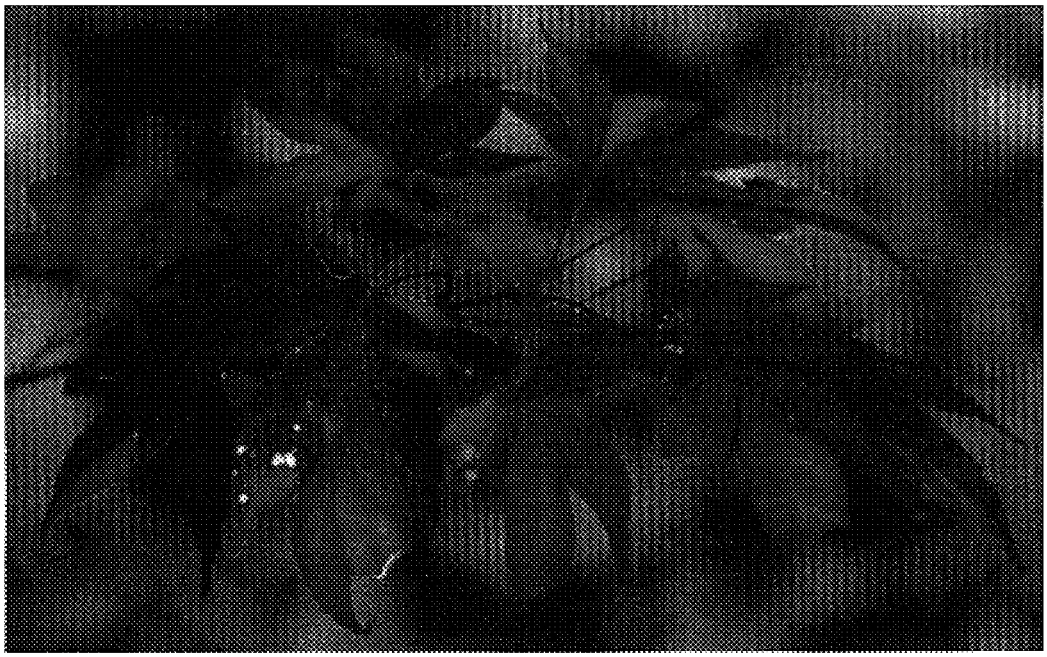

* * * * *